(12) United States Patent
Gündel

(10) Patent No.: US 8,351,564 B2
(45) Date of Patent: Jan. 8, 2013

(54) METHOD FOR DISPLAYING IMAGE DATA OF A LARGE INTESTINE OF A PATIENT ON THE BASIS OF TOMOGRAPHIC EXAMINATION DATA

(75) Inventor: Lutz Gündel, Erlangen (DE)

(73) Assignee: Siemens Aktiengesellachaft, Munich (DE)

( * ) Notice: Subject to any disclaimer, the term of this patent is extended or adjusted under 35 U.S.C. 154(b) by 659 days.

(21) Appl. No.: 12/461,996

(22) Filed: Aug. 31, 2009

(65) Prior Publication Data
US 2010/0067763 A1    Mar. 18, 2010

(30) Foreign Application Priority Data
Sep. 1, 2008   (DE) .......................... 10 2008 045 342

(51) Int. Cl.
*A61B 6/00* (2006.01)
*G06K 9/00* (2006.01)

(52) U.S. Cl. ............. 378/4; 378/5; 378/98.11; 382/128; 382/131

(58) Field of Classification Search .................. 382/128, 382/131; 378/4, 5
See application file for complete search history.

(56) References Cited

U.S. PATENT DOCUMENTS

| | | | |
|---|---|---|---|
| 5,690,106 A * | 11/1997 | Bani-Hashemi et al. | 600/425 |
| 5,782,762 A * | 7/1998 | Vining | 600/407 |
| 6,996,205 B2 | 2/2006 | Avinash | |
| 7,035,681 B2 * | 4/2006 | Johnson et al. | 600/420 |
| 7,876,947 B2 * | 1/2011 | Lee et al. | 382/131 |
| 7,965,880 B2 * | 6/2011 | Yoshida et al. | 382/128 |
| 8,131,036 B2 * | 3/2012 | Collins et al. | 382/128 |
| 2002/0097320 A1 * | 7/2002 | Zalis | 348/65 |
| 2004/0101183 A1 * | 5/2004 | Mullick et al. | 382/131 |
| 2005/0201601 A1 * | 9/2005 | Sun et al. | 382/128 |
| 2006/0109953 A1 * | 5/2006 | Walter et al. | 378/5 |
| 2006/0215896 A1 * | 9/2006 | Sirohey et al. | 382/131 |
| 2007/0073114 A1 * | 3/2007 | Gundel | 600/300 |
| 2007/0116346 A1 * | 5/2007 | Peterson et al. | 382/131 |
| 2007/0127804 A1 * | 6/2007 | Yoshida et al. | 382/131 |
| 2008/0228067 A1 * | 9/2008 | Truyen | 600/425 |
| 2008/0273781 A1 * | 11/2008 | Manduca et al. | 382/131 |

FOREIGN PATENT DOCUMENTS
WO    WO 2007046019 A1    4/2007

* cited by examiner

*Primary Examiner* — Alexander H Taningco
(74) *Attorney, Agent, or Firm* — Harness, Dickey & Pierce, P.L.C.

(57) ABSTRACT

A method is disclosed for displaying image data of a large intestine of a patient on the basis of tomographic examination data. In at least one embodiment, the method includes scanning of the patient, after ingestion of a contrast agent, in at least two differently aligned positions using a tomography system and generating a tomographic image data record for each position; segmenting the large intestine in the tomographic data records; detecting and marking regions of the segmented large intestine with adjacent remaining stool in the intestine (covered regions); registering the segmented large intestine in the at least two tomographic image data records; displaying a tomographic display of the segmented large intestine including markings of the covered regions; and displaying a selection menu in which tomographic displays of the segmented large intestine in the at least two differently aligned positions of the patient, including a marking of the covered regions, can be selected alternatively.

18 Claims, 3 Drawing Sheets

METHOD FOR DISPLAYING IMAGE DATA OF A LARGE INTESTINE OF A PATIENT ON THE BASIS OF TOMOGRAPHIC EXAMINATION DATA

PRIORITY STATEMENT

The present application hereby claims priority under 35 U.S.C. §119 on German patent application number DE 10 2008 045 342.0 filed Sep. 1, 2008, the entire contents of which are hereby incorporated herein by reference.

FIELD

At least one embodiment of the invention generally relates to a method for displaying image data of a large intestine of a patient on the basis of tomographic examination data, in particular on the basis of CT and/or MRI data, with the examiner being provided with differently prepared image data for evaluation purposes depending on the perceptibility and relevance of an examination region.

BACKGROUND

Tumorous disease of the large intestine and the precursors thereof are relatively common these days. Flexible endoscopy is usually used for preferably prophylactic examination of this disease. Since the examination has been licensed by now as a screening examination, it significantly contributes to the prevention of and reduction in the mortality in colorectal carcinoma. However, its level of acceptance as a primary diagnostic tool is insufficient due to the discomfort of the patient connected therewith. A noninvasive diagnostic tool for the large intestine would find significantly higher acceptance. Virtual colonography on the basis of CT or MRI data is known in principle and overall offers much more than flexible endoscopy since the intestinal wall thickness, fat lamellae, infiltration depths, perfusion and lymph nodes can also be assessed without restrictions in the same session.

A significant aspect in this case is to enhance the acceptance of the examination, without simultaneously decreasing the sensitivity of examination and increasing the complexity for evaluation purposes.

SUMMARY

In at least one embodiment of the invention, a method is disclosed for displaying image data of a large intestine of a patient on the basis of tomographic examination data, which supplies base data to a user in a simple and secure manner for a diagnostic evaluation.

The following has been recognized by the inventor: Patients perceive rigorous discharge of the contents of the intestine to be uncomfortable although it is optimal with regard to the image quality for evaluation of the large intestine using virtual colonography. This is one reason why this established method has such low acceptance by patients. The method of stool tagging (=marking the stool using a contrast agent) avoids the uncomfortable procedure. In this case, the patient receives a special diet and liquid, laced with a contrast agent, two days before the examination. The remaining stool and the contrast agent admix. The mixture now is easily recognizable in image data records reconstructed from CT or MRI data, with different contrast agents being utilized in accordance with the detection method used.

It is possible for both multi-planar reconstructions and three-dimensional views to be calculated from the reconstructed tomographic data records. In multi-planar reconstructions, the observer can easily differentiate between the contents of the intestine and the intestinal tissue which is actually of interest. However, evaluation on the basis of multi-planar reconstructions takes up a lot of time, particularly if the stool has not mixed homogeneously with the contrast agent. Lesions covered by the remaining stool can easily be overlooked and therefore these regions have to be examined particularly meticulously. A simpler, and in particular faster, evaluation can be achieved with the aid of a virtual flight through the three-dimensional illustration of the intestine. However, in this case the remaining stool is bothersome because parts of the intestinal surface cannot be seen. It is known to digitally remove the bothersome remaining stool using digital stool subtraction. However, the disadvantage of this method is that artifacts which look similar to the sought after lesions are frequently generated and this can lead to undesired erroneous diagnoses in the subsequent evaluation.

In the following text, a method is described in at least one embodiment which recognizes the intestinal surface covered by remaining stool and marks it in an illustration. Furthermore, in accordance with this method, at least two measurements, preferably in prone and dorsal positions, are carried out and the two reconstructed data records are first of all analyzed independently. Subsequently, a check is made and visualized for the user as to which intestinal surfaces can be seen in at least one data record (and preferably in which one as well), or which cannot be seen in any data record. The method can now automatically start a virtual flight as soon as this is possible as a result of clearly recognizable intestinal surfaces and useful for evaluation purposes; otherwise it is also possible to automatically switch to displaying a slice image as soon as intestinal regions with remaining stool are reached so that a better diagnostic view is made possible in this case. Alternatively, the desired view can also be selected manually.

Thus, the user can use this system to evaluate the greatest possible surface of the intestine using a virtual flight. The multi-planar reconstruction method, which requires more time, would in this case only have to be viewed in a small section. In any case, it is ensured that 100% of the intestinal surface can be diagnosed in an optimum fashion.

Accordingly, the inventor proposes a method, in at least one embodiment, for displaying image data of a large intestine of a patient on the basis of tomographic examination data, comprising:
  ingestion of a contrast agent by the patient,
  scanning of the patient in at least two differently aligned positions using a tomography system and generating a tomographic image data record for each position,
  segmenting the large intestine in the tomographic data records,
  detecting and marking regions of the segmented large intestine with adjacent remaining stool in the intestine (=covered regions),
  registering the segmented large intestine in the at least two tomographic image data records,
  displaying a tomographic display of the segmented large intestine including markings of the covered regions, and
  displaying a selection menu in which tomographic displays of the segmented large intestine in the at least two differently aligned positions of the patient, including a marking of the covered regions, can be selected alternatively.

It can be advantageous for the covered regions to be marked in a data-record specific fashion. This allows the user in each case to select one of the at least two data records in which the covered regions are as small as possible.

Furthermore, a virtual flight through the large intestine can be displayed for evaluation purposes, with only image data from uncovered regions being shown in the virtual flight and with slice images automatically being displayed for evaluation purposes in large intestine sections which have no uncovered regions available.

Advantageously, the percentage of uncovered regions and/or covered regions can be displayed for every data record. Furthermore, the percentage of the intestine surface for which an uncovered region exists in any data record and/or for which only covered regions are available in all data records can be displayed. Using this, the user can already recognize in an overview whether the present method can be used in a meaningful manner, or whether a complete evaluation using only multi-planar reconstructions should be selected because too many intestinal surfaces are covered.

Furthermore, provision is made for a safety margin which can be specified around the covered regions, from where a transition is made from the display of a virtual flight to displaying a slice image. Accordingly, it is also possible to specify a minimum length which an intestinal segment has to have for it to be shown in the virtual flight.

The above-described method can be used in particular with X-ray CT data, with air or $CO_2$ being used as a contrast agent and for filling the intestine. Semi-solid food containing barium or iodine is administered to the patient before the examination in order to mark the stool.

The method can also be used in combination with nuclear magnetic resonance data, or the latter can be used as an alternative, with water in this case being preferably used for filling the intestine and as a contrast agent.

A computational unit for preparing tomographic data records having a storage for storing computer programs, wherein in the storage there are computer programs which execute at least one embodiment of the method described above during operation, is also included within the scope of at least one embodiment of the invention.

BRIEF DESCRIPTION OF THE DRAWINGS

In the following text, the invention will be explained in more detail on the basis of an example embodiment and with the aid of the figures, with only the features required for understanding the invention being illustrated. Here, the following reference symbols are used: 11: generating a first tomographic data record I; 12: segmenting; 13: detecting the stool; 14: detecting the surface; 15: determining the surface covered by stool; 16: determining the surface not covered by stool; 21: generating a second tomographic data record II; 22: segmenting; 23: detecting the stool; 24: detecting the surface; 25: determining the surface covered by stool; 26: determining the surface not covered by stool; 30: registering; 31: controlling the display of the examined intestine; 32: output of the proportion of covered surfaces; 33: preparing the output of multi-planar reconstructions, possibly with marking covered surfaces; 34: switch between virtual flight and displaying a slice image; 35: screen dump; 36: switch between data record I and II during the virtual flight; 37: virtual flight; I: first data record; II: second data record; C1: CT system; C2: first X-ray tube; C3: first detector; C4: second X-ray tube (optional); C5: second detector (optional); C6: gantry housing; C7: patient; C8: examination couch; C9: system axis; C10: control and computational unit; C11: storage; M1: MRI system; M2: magnetic coils; M3: receiver coils; M4: gradient coils; M6: housing; M10: control and computational unit.

In detail.

DETAILED DESCRIPTION OF THE EXAMPLE EMBODIMENTS

Figure 1:
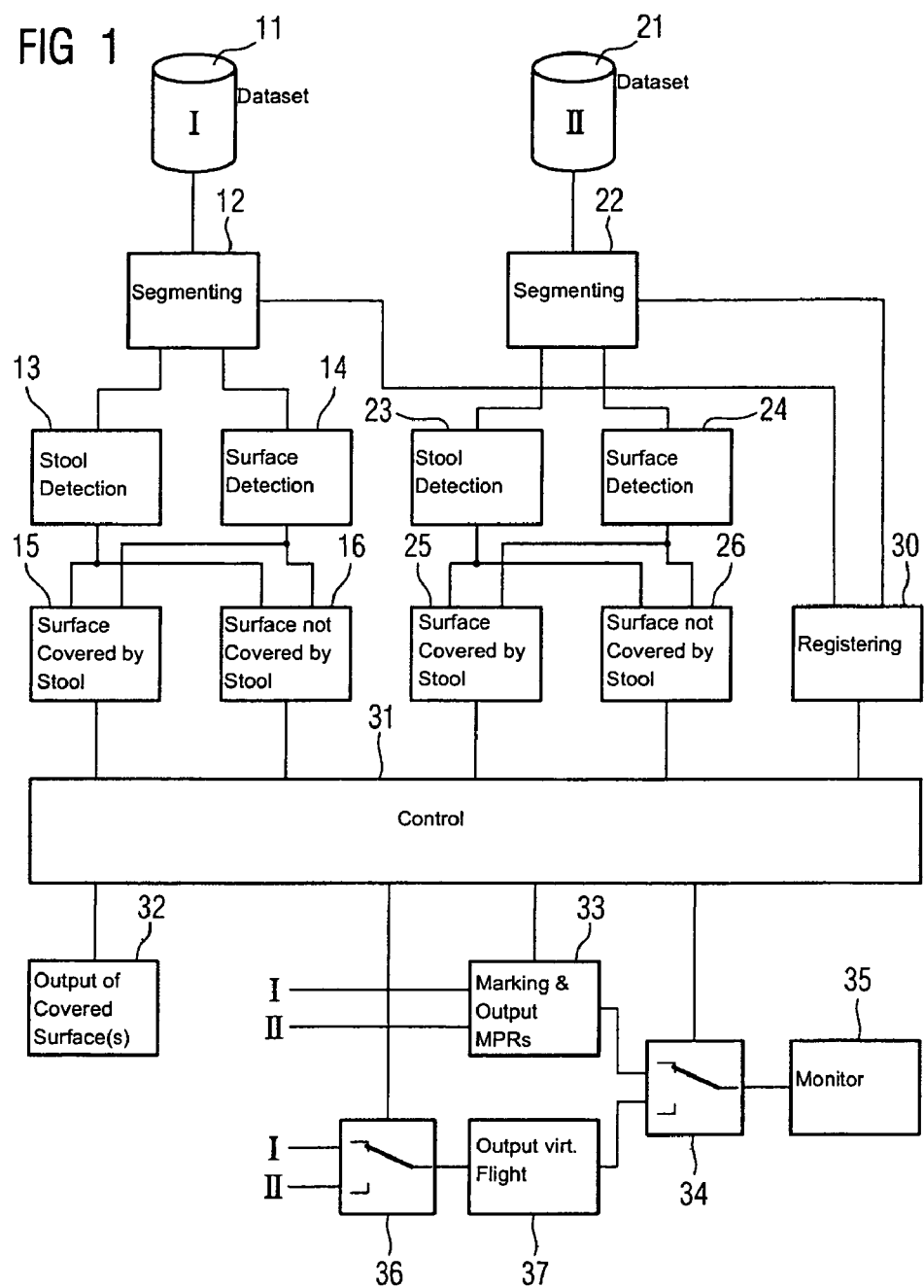
FIG. 1 shows a flowchart of a method according to an embodiment of the invention in virtual colonography.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a flowchart of an example method in virtual colonography according to the invention. Here, the intestinal surface of a patient is examined using virtual flight, with regions of the intestine where the view of the intestinal wall is obscured by remaining stool automatically being displayed in a slice image so that an optimal safe evaluation of the intestinal surface is always ensured.

Two data records I, reference symbol 11, and II, reference symbol 21, from two different positions of a patient, for example from prone and dorsal positions, of a CT or MRI examination are available to this method. The data records are in principle treated in the same fashion, with two processing lines 11-16 and 21-26 being created. The data records 11 and 21 are first of all subject to segmenting 12 and 22, from which a 3D data record of the intestine is obtained in a known fashion for each processing line. Now, the remaining stool which is also segmented is detected 13 and 23 in these data records; and in parallel, the intestinal surface is determined in parallel steps 14 and 24. The positional information of the intestinal surface and the remaining stool can be used in steps 15, 25 and 16, 26 to determine the regions of the intestine where the surface is covered by remaining stool and the regions where the surface can be seen without obstruction. Additionally, the segmented intestine is registered in method step 30 so that it is possible to compare the surfaces determined in steps 15, 16 and 25, 26.

It should also be mentioned that when the size of the covered or uncovered surface is determined, a minimum size of a mark above which it is intended to be evaluated as covered can additionally be specified as a criterion. This affords the possibility of ignoring small covered areas which are not diagnostically relevant in the evaluation. Usually sizes are used in this case which are significantly smaller than sought after changes in the intestinal surface, i.e. which are for example significantly smaller than the size of a typical polyp.

All this information is now supplied to the control unit 31 of the visualization, with it now also being possible to determine and visualize here which regions of the intestine can be seen without obstruction in at least one data record I or II and which regions of the intestine cannot be seen without obstruction in either of the data records I and II and hence necessitate displaying a slice image for evaluation purposes. The control unit 31 now outputs for the user the covered surfaces of the individual data records and the surfaces covered in both data records by displaying the corresponding regions differently in an illustration of the intestine.

During the subsequent virtual flight 37, only the uncovered segments are output on the screen. If the user flies into an intestinal section in which both data records are covered by stool, these are marked and displayed in the multi-planar reconstructions (MPR).

Additionally, the display control is illustrated schematically below the control unit 31. Here, starting from the two available data records I and II, the switch 36 is firstly used to select one of the two 3D displays which can be displayed in the virtual flight in accordance with step 37, or which can be displayed the best. Here, the size of the surface not covered by stool serves as a criterion. If it is impossible to display a virtual flight over an uncovered surface using data records I and II, the switch 34 is used to switch to displaying a slice image (upper path). Here, both slice images of data records I and II are prepared for display in step 33 and output on the screen 35 in accordance with the position of the switch 34. Alternatively, it is also possible to switch between the slice images from data records I and II before step 33, with the display of the slice image with a larger proportion of uncovered surface being automatically selected in this case. Additionally, a switch which is to be operated manually by the observer can alternatively be used to let the user arbitrarily select one of the two multi-planar reconstructions.

In detail, the abovementioned method steps are effected as follows:

Segmenting the intestine in steps 12 and 22: Here, the large intestine is firstly extracted from the two reconstructed data records I and II in a known fashion. The contrast agents, e.g. water in MRI examinations or air or carbon dioxide in CT examinations, permit simple segmenting of the large intestine. However, if contrast agent passes from the large intestine to the small intestine during the examination, the latter is also segmented. This is undesirable and these portions can additionally be deleted interactively.

Remaining stool detection in steps 13 and 23: Remaining stool, which is admixed with the additionally orally supplied barium- or iodine-containing contrast agent, has a significantly higher attenuation value (e.g. 300 HU) than the surrounding intestinal tissue (e.g. 100 HU to+100 HU) in the tomographic data of a CT system and hence it can be detected by thresholding. Since the attenuation value depends on the amount of dispensed contrast agent, a variable threshold should be used in this case. Inhomogeneities in the stool/contrast agent mixture lead to the threshold being undershot during the thresholding and individual voxels or clusters of a few voxels are mistakenly not recognized as remaining stool. This can be compensated for in the successfully detected regions by using the known "closing" or "region growing" methods.

Surface detection as per method steps 14 and 24. The transitions between air and intestinal tissue (<−800 HU to −100 . . . +100 HU) and between remaining stool (e.g. 300 HU) and intestinal tissue determine the intestinal surface. The transitions are not abrupt; depending on the reconstruction kernel used, they can be a number of voxels.

Determining the intestinal surfaces which are covered/not covered by remaining stool in steps 14 and 24: The covered and uncovered portions of the intestinal surface are obtained from the overall surface of the intestine and the detected stool on the basis of the obtained positional information of the remaining stool and intestinal wall. Accordingly, the covered and uncovered regions of the intestinal surface are determined in steps 15, 16 and 25, 26 and passed on to the control unit 31.

Registration as per step 30: In principle, different methods of registration using rigid or non-rigid algorithms are known. Registration is necessary because the large intestine can move between the other organs of the abdominal cavity and the movement of the patient between two examinations markedly changes the latter's anatomy. During the examination, the large intestine is filled with water (MRI) or air or carbon dioxide (CT) which is differently distributed in the intestine in the two positions of the patient. The parts which are not filled, which differ from examination to examination, have collapsed and the intestine can only be segmented in those partial segments which have not collapsed. In this case, using central lines in the registration is particularly advantageous. These central lines are either the middle lines or the flight paths along which the virtual flight is carried out.

If parts of the intestine have collapsed, the central lines which have also been interrupted must be connected to one another.

Since the registration is not precise in most cases, if one position in one data record is considered, the corresponding position in the other data record can only be found approximately. An embodiment of the present method can take account of this by, for example, using safety margins. What is achieved by using these safety margins when defining regions which cannot be seen without obstruction is that such regions which cannot be seen without obstruction are not overlooked in the evaluation as a result of imprecise registration.

Figure 2:
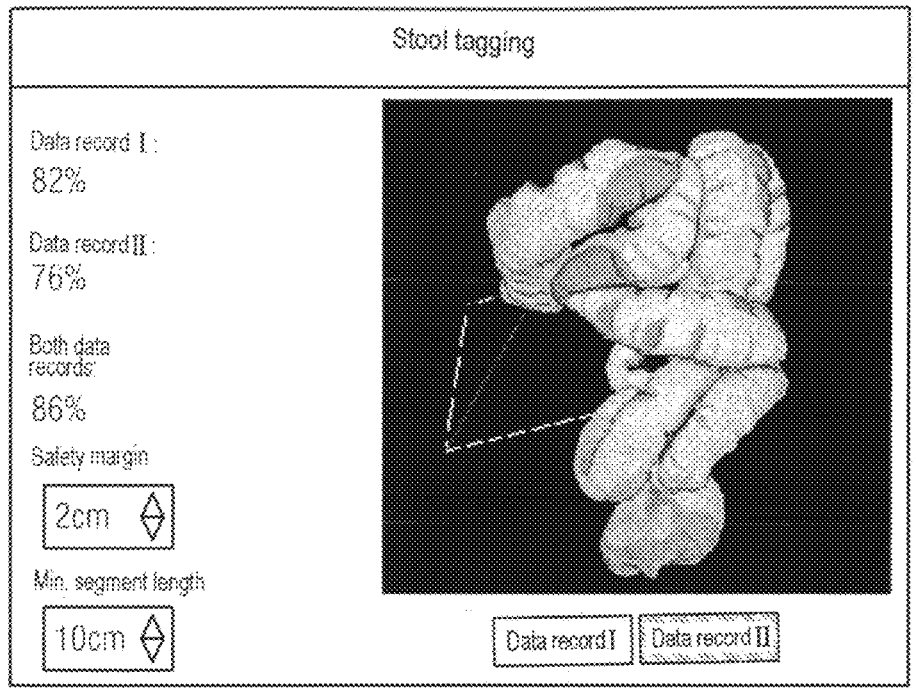
FIG. 2 shows a screen dump at the start of the virtual colonography with a 3D illustration of a large intestine.
Figure 3:
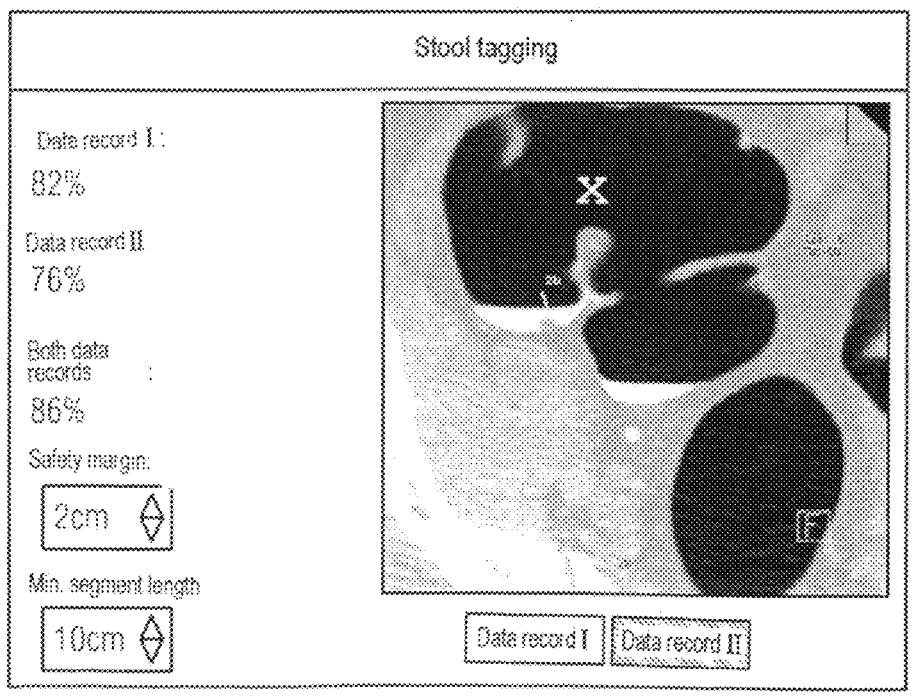
FIG. 3 shows a screen dump in the region of a covered intestinal surface, with a colon displayed as a slice image.

Now, FIGS. 2 and 3 show two exemplary screen dumps in accordance with the method step 35 from FIG. 1. FIG. 2 shows the screen with a user interface, where the percentage of the region of the intestine which can be seen without obstruction in data records I and II is shown on the left, and, below that, the percentage of the region in which the intestinal surface can be seen without obstruction in at least one of the two data records. In data record I, 82% of the surface can be seen without obstruction and in data record II it is only 76%. If the data records are combined, this results in a free surface of 86% in total. The three-dimensional display of the intestine shows the marked regions, which cannot be seen without obstruction from both positions, projected onto the segmentation result from data record I in a volume rendering display. Alternatively, data record II can also be selected in this case. In a variant, it is also possible for the free or the covered surfaces of the individual data records to be visualized separately.

If the user selects a virtual flight for evaluation purposes due to the percentages, said virtual flight is started using e.g. data record I. The flight is now continued on the central line of the intestine using this data record until a region covered by stool is reached. If there is a continuing region in data record II with a length which is greater than the prescribed minimum segment length, 10 cm in this case, and which can be seen without obstruction in the corresponding position, then a switch is made to data record II and the flight is continued there. However, during the switch, the flight is moved back in the intestine by an amount equaling the safety margin, 2 cm in this case, to ensure that no region of the intestine is exempt from the evaluation, even in the case of a not quite correct registration.

If there is no sufficiently long segment without cover available in the second data record when a covered region is reached in the virtual flight, a switch is automatically made to display a slice image of these regions. Such a situation is shown in FIG. 3. Here, the intestinal region with remaining stool present is shown using a multiplicity of advancing slices which are preferably always aligned perpendicularly to the central line of the intestine.

As soon as a sufficiently long intestinal segment without cover is reached again in either of the two data records, the method again switches to the virtual flight display in the corresponding data record which can be evaluated more quickly.

Figure 4:
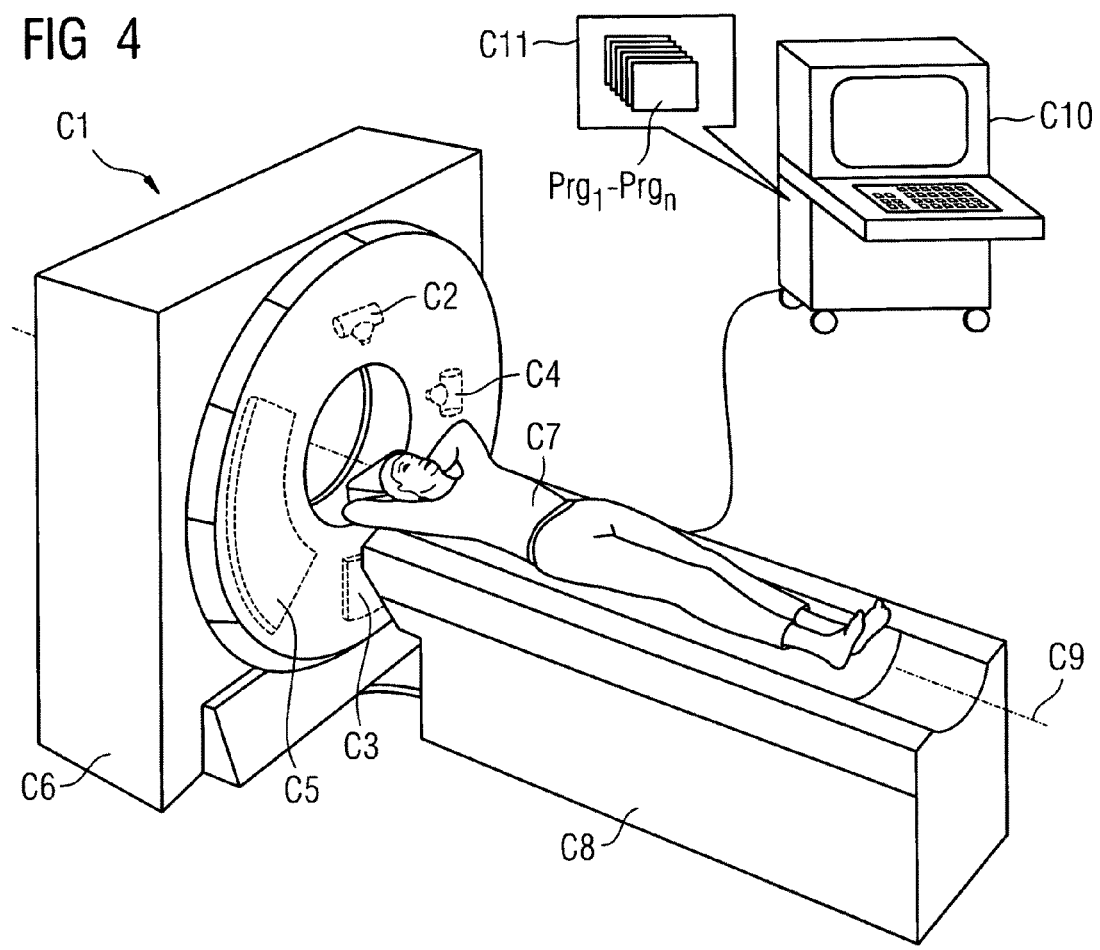
FIG. 4 shows a CT system for using the method according to an embodiment of the invention.
Figure 5:
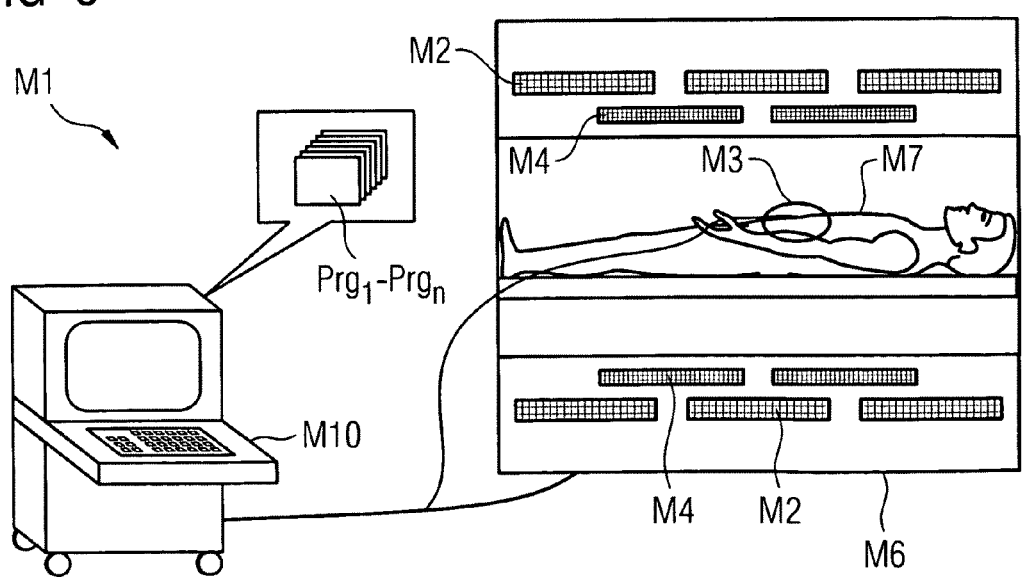
FIG. 5 shows an MRI system for using the method according to an embodiment of the invention.

FIGS. 4 and 5 respectively show an exemplary CT system and MRI system which can be used to carry out the method described above.

The CT system C1 in FIG. 4 has a first tube/detector system with an X-ray tube C2 and an opposing detector C3. Optionally, this CT system C1 can also comprise a second X-ray tube C4 with an opposing detector C5. This also affords the possibility of simultaneously carrying out the respective scan using different X-ray spectra, which makes differentiated recognition of different materials possible. This may also make it possible to dispense with using a contrast agent, or use a more tolerable contrast agent. Both tube/detector systems are located on a gantry which is arranged in a gantry housing C6 and rotates around a system axis C9 during the scan. The patient C7 is on a displaceable examination couch C8 which, during the scan, is pushed in either a continuous or sequential fashion along the system axis C9 and through the scanning field located in the gantry housing C6. This makes it possible for the detectors to measure the attenuation of the X-rays emitted by the X-ray tubes in a spiral scan or a sequential circular scan.

The CT system C1 is controlled using a control and computational unit C10 which stores computer programs $Prg_1$ to $Prg_n$ which, during operation, are able to also execute the above-described method according to an embodiment of the invention. Additionally, this control and computational unit C10 can also output image data. However, reference is made to the fact that the method according to the invention can also be executed on a separate data processing terminal as soon as the required tomographic data records are available there. This makes it possible to decouple the evaluation from the tomographic examination in terms of work.

The method according to an embodiment of the invention can also be executed using tomographic data from an MRI system. Such a magnetic resonance imaging system (MRI system) M1 is illustrated in FIG. 5. In this MRI system M1, a housing M6 holds magnetic coils M2 for generating a strong magnetic basic field, as a result of which the hydrogen nuclei in the body of the patient are aligned parallel or anti-parallel to the magnetic field lines in accordance with their spin. Using an alternating electromagnetic field at the resonance frequency of the atomic nuclei to excite the atomic nuclei causes the latter to oscillate. Once the excitation frequency has been switched off, the atomic nuclei return to their original state and emit their oscillation energy in the form of electromagnetic oscillation energy which is measured using receiver coils M3. Additional magnetic coils M4 generate a weak magnetic field with a defined field gradient, as a result of which the signals emitted by the nuclei comprise locational information by means of which the position of the emitted signal can be defined. The control and computational unit M10 controls this system M1 and evaluates the measurement signals, said control and computational unit having programs $Prg_1$ to $Prg_n$ in its storage which also execute the method according to an embodiment of the invention in addition to the control and the image calculation.

In this case, it is also possible for the method according to an embodiment of the invention to be executed on a separate data processing terminal, as soon as the necessary tomographic data records are available there, such that the evaluation can be decoupled from the tomographic examination in terms of work.

It is understood that the abovementioned features of the invention can be used not only in the respectively specified combination but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for displaying image data of a large intestine of a patient on the basis of tomographic examination data, comprising:
    scanning the patient, after ingestion of a contrast agent, in at least two differently aligned positions using a tomography system and generating a tomographic image data record for each of the at least two positions;
    segmenting the large intestine in the tomographic data records;
    detecting and marking regions of the segmented large intestine having adjacent remaining stool in the intestine, the marked regions being covered regions;
    registering the segmented large intestine in the at least two tomographic image data records;
    displaying a tomographic display of the segmented large intestine including the marking of the covered regions; and
    displaying a selection menu in which tomographic displays of the segmented large intestine in the at least two differently aligned positions of the patient, including the marking of the covered regions, are alternatively selectable.

2. The method as claimed in claim 1, wherein the covered regions are marked in a data-record specific fashion.

3. The method as claimed in claim 2, wherein a virtual flight through the large intestine is displayed for evaluation purposes, with only image data from uncovered regions being shown in the virtual flight and with slice images automatically being displayed for evaluation purposes in large intestine sections which have no uncovered regions available.

4. The method as claimed in claim 3, wherein the percentage of at least one of uncovered regions and covered regions is displayed for every data record.

5. The method as claimed in claim 2, wherein the percentage of at least one of uncovered regions and covered regions is displayed for every data record.

6. The method as claimed in claim 1, wherein a virtual flight through the large intestine is displayed for evaluation purposes, with only image data from uncovered regions being shown in the virtual flight and with slice images automatically being displayed for evaluation purposes in large intestine sections which have no uncovered regions available.

7. The method as claimed in claim 6, wherein the percentage of at least one of uncovered regions and covered regions is displayed for every data record.

8. The method as claimed in claim 1, wherein the percentage of at least one of uncovered regions and covered regions is displayed for every data record.

9. The method as claimed in claim 8, wherein the percentage of the intestine surface at least one of for which an uncovered region exists in any data record and for which only covered regions are available in all data records is displayed.

10. The method as claimed in claim 1, wherein a safety margin is specifiable around the covered regions, from where a transition is made from the display of a virtual flight to displaying a slice image.

11. The method as claimed in claim 10, wherein it is possible to specify a minimum length which an intestinal segment has to have for it to be shown in the virtual flight.

12. The method as claimed in claim 1, wherein the method is used in combination with X-ray CT data.

13. The method as claimed in claim 12, wherein barium or iodine is used as a contrast agent.

14. The method as claimed in claim 1, wherein the method is used in combination with nuclear magnetic resonance data.

15. The method as claimed in claim 14, wherein water is used as a contrast agent.

16. The method as claimed in claim 1, wherein the method is used in combination with both X-ray CT data and nuclear magnetic resonance data.

17. A computational unit for preparing tomographic data records, comprising:
   a storage to store computer programs to execute the method as claimed in claim 1.

18. A non-transitory computer readable medium including program segments for, when executed on a computer device, causing the computer device to implement the method of claim 1.

* * * * *